(12) United States Patent
Lundell et al.

(10) Patent No.: US 6,883,199 B1
(45) Date of Patent: Apr. 26, 2005

(54) SHORT-LIFE POWER TOOTHBRUSH FOR TRIAL USE

(75) Inventors: William G. Lundell, Issaquah, WA (US); Daniel Bayeh, Seattle, WA (US); Jane M. Mueller, Bellevue, WA (US); John W. Pace, Bothell, WA (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 376 days.

(21) Appl. No.: 09/588,807

(22) Filed: Jun. 6, 2000

(51) Int. Cl.[7] .................................................. A61C 17/22
(52) U.S. Cl. ........................................ 15/22.1; 310/273
(58) Field of Search ................................ 15/22.1–22.4, 15/23–24, 28–29; 310/1, 15, 273

(56) References Cited

U.S. PATENT DOCUMENTS

| 3,220,039 A | 11/1965 | Dayton et al. ................. 15/28 |
| 4,179,814 A | * 12/1979 | Montanio .................. 15/23 X |
| 5,189,751 A | * 3/1993 | Giuliani et al. ............... 15/22.1 |
| 5,994,855 A | 11/1999 | Lundell et al. ............. 318/114 |
| 6,000,083 A | 12/1999 | Blaustein et al. .............. 15/28 |
| 6,230,717 B1 | * 5/2001 | Marx et al. ................. 15/28 X |

FOREIGN PATENT DOCUMENTS

| EP | 1095630 A2 | 5/2001 |
| FR | 2680086 | 2/1993 |

* cited by examiner

*Primary Examiner*—Mark Spisich

(57) ABSTRACT

A trial (test) power toothbrush designed to emulate the performance of a corresponding commercial toothbrush, powered by a non-rechargeable battery. The power to drive the toothbrush is controlled by a control circuit which is responsive to the battery to maintain the drive power at approximately the level of the commercial unit and a short "trial use" period, i.e. one month/30 days, and then to terminate operation of the power toothbrush. The trial toothbrush may then be readily disposed of by the user, including the battery therein.

10 Claims, 3 Drawing Sheets

SHORT-LIFE POWER TOOTHBRUSH FOR TRIAL USE

TECHNICAL FIELD

This invention relates generally to power toothbrushes and more specifically concerns power toothbrushes which are designed for a limited time trial use:

BACKGROUND OF THE INVENTION

Conventional power toothbrushes are typically expensive, especially compared with the cost of manual toothbrushes, often as much as 20–30 times that of a manual toothbrush. It is accordingly difficult to persuade many people to buy a power toothbrush because of the high price and the fact that there is no opportunity to try the power toothbrush without a price risk. Yet, it is believed by many power toothbrush manufacturers that if a potential buyer gives a power toothbrush a fair trial use, a significant chance exists that a sale of the power toothbrush will occur, particularly if, during the trial use, the toothbrush. demonstrates a good cleaning effect and a good "feel" following use. Manufacturers of power toothbrushes up to this point, however, have not attempted to provide a trial-type power toothbrush to the public for a limited time, trial use. It is unknown as to whether this is because of cost or other considerations. It is actually uncertain as to whether any manufacturers have even considered the use of a special trial unit to promote power toothbrushes.

Persuading potential customers to purchase a power toothbrush has thus been left to marketing efforts or testimonials from others, as well as recommendations from dental professionals. While these techniques have certainly met with some success, particularly for certain power toothbrushes, a very large segment of the total toothbrush market remains untapped for power toothbrushes. A substantial percentage of this segment can perhaps only be convinced if they are able to try the power toothbrush risk-free for a certain period of time. One group of customers may need the trial device to convince them; without it they may never purchase a commercial power toothbrush. Another group of customers might conceivably use a trial unit to accelerate their decision to purchase a power toothbrush. The challenge to the manufacturer is to design a "trial-type" (test unit) power toothbrush which fundamentally emulates a corresponding conventional (standard) unit for a short period of time by providing an equivalent brushing experience and benefits, the trial unit thereafter being completely disposable.

SUMMARY OF THE INVENTION

Accordingly, the present invention is a disposable, trial-use power toothbrush, comprising: a trial power toothbrush designed to emulate the performance of a corresponding commercially available power toothbrush; a power system to provide power for the trial power toothbrush for only a selected short period of time which is long enough that the user becomes accommodated to the operation of the trial power toothbrush and can evaluate the performance thereof, wherein the trial power toothbrush approximates the operation of the corresponding commercial toothbrush for said selected period of time and wherein when the trial power toothbrush is no longer operational following said selected period of time, the trial power toothbrush may be disposed of.

BEST MODE FOR CARRYING OUT THE INVENTION

Figure 1:
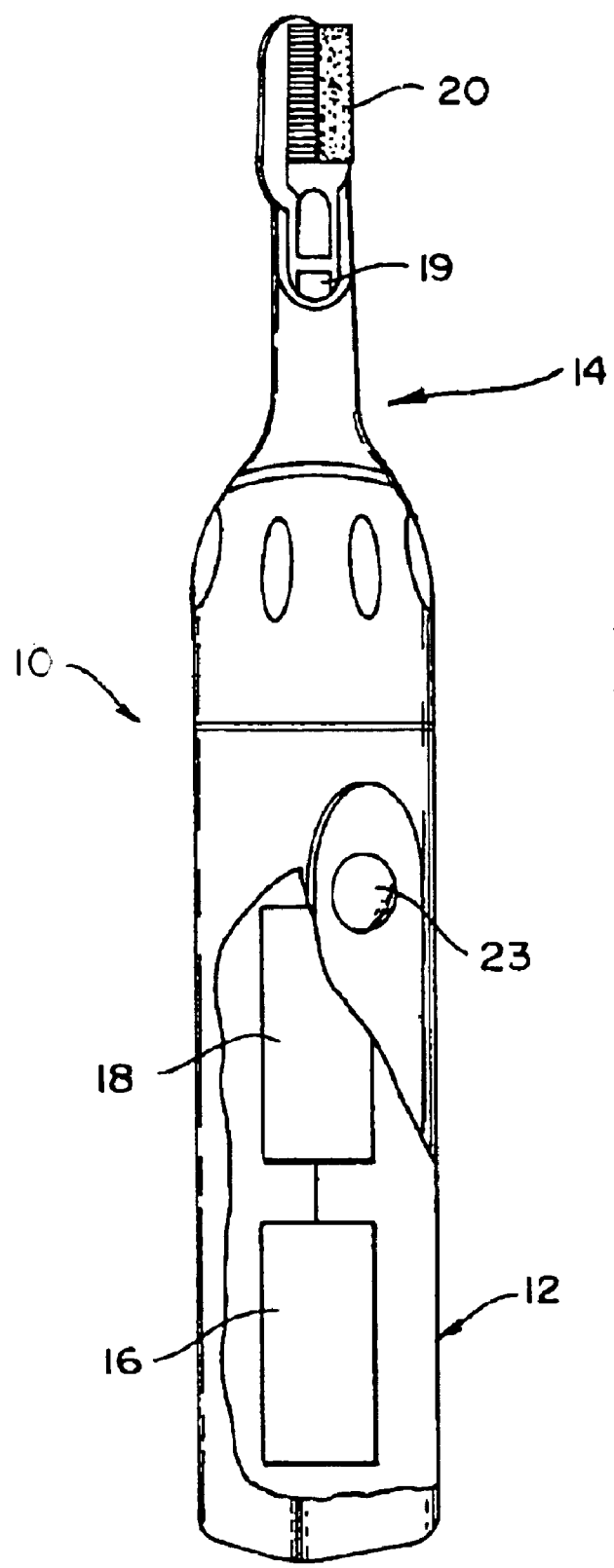
FIG. 1 is a simplified schematic view of a power toothbrush showing the major component parts thereof.

The trial power toothbrush unit of the present invention is shown in schematic form in FIG. 1. The trial power toothbrush concept is described in accordance with a particular power toothbrush arrangement for purposes of explanation. However, it should be understood that the principles of the present invention can be applied to power toothbrushes of various designs and arrangements. Specifically, it should be understood that the principles of the present invention are not limited to the specific toothbrush structure shown and described in detail herein.

The corresponding commercial toothbrush of FIG. 1 is actually shown and described in U.S. Pat. No. 5,994,855, and in more detail in U.S. Pat. No. 5,189,751, both of which are owned by the assignee of the present invention. The trial toothbrush unit is shown generally at 10 and includes a handle portion 12 and a head portion 14 which is removable from the handle portion. Handle portion 14 includes a battery 16 and an electromagnetic motor 18. Head portion 14 includes an elongated vibrating resonant arm 19, at the forward end of which is a brushhead 20. The resonant arm 19 is mounted on a cross-wise positioned torsion pin and is driven in a back and forth motion by motor. 18. The unit is controlled by on-off switch 23. The trial toothbrush unit 10 of the present invention is designed and constructed to emulate the operation and performance of a corresponding commercial unit.

The important concept of the present invention is that the trial unit emulate the performance of the corresponding commercial unit. As mentioned above, the invention is not limited to a particular configuration of trial unit or commercial unit.

The commercial toothbrush which is emulated by the trial unit of FIG. 1 is powered by two rechargeable nickel cadmium batteries of 1.2 volts each. Other rechargeable batteries could be used in the commercial unit. The rechargeable batteries in the commercial unit are typically not disposable and are recharged by a companion charger unit.

In the trial unit 10 of the present invention, the batteries 16 are non-rechargeable, disposable batteries. No charger is included with the trial unit. Typically, the batteries 16 are two 1.5 volt alkaline batteries. Hence, it is necessary in the embodiment shown to initially decrease the level of battery voltage output applied to the motor to emulate the commercial unit. In this case, the voltage level of the alkaline batteries 16 must be decreased to the voltage level of the rechargeable batteries in the commercial unit.

In addition, the trial unit 10 of the present invention, in order to fully emulate the commercial unit, includes a particular adaptive feature also present in the corresponding commercial unit, wherein the initial series of uses of the toothbrush are at a lower than full power level, to permit a period of adjustment to the feel of the power toothbrush and its effect on the gums and teeth.

The batteries of the trial unit 10 of the present invention, in combination with a power control circuit, are designed to provide approximately full power (comparable to the commercial unit) for approximately only one month's usage. One month's (30 days) usage, i.e. 60 brushings, is believed to be an appropriate time for a fair trial of the toothbrush, although it should be understood that somewhat more or fewer uses could be selected. The entire trial unit 10 is disposable after the trial time has passed.

The batteries 16 have enough power capacity to last for an adequate trial, i.e. one month/30 days. Typically, one month allows approximately two weeks for the user to get used to the operation and feel of the toothbrush and then two weeks to get the full effect and benefit of the toothbrush. A month (30 days) will typically be sufficient for an adequate trial for most users; at the end of the trial time, the user will hopefully experience sufficient benefits and effects to purchase the corresponding commercial device.

Figure 3:
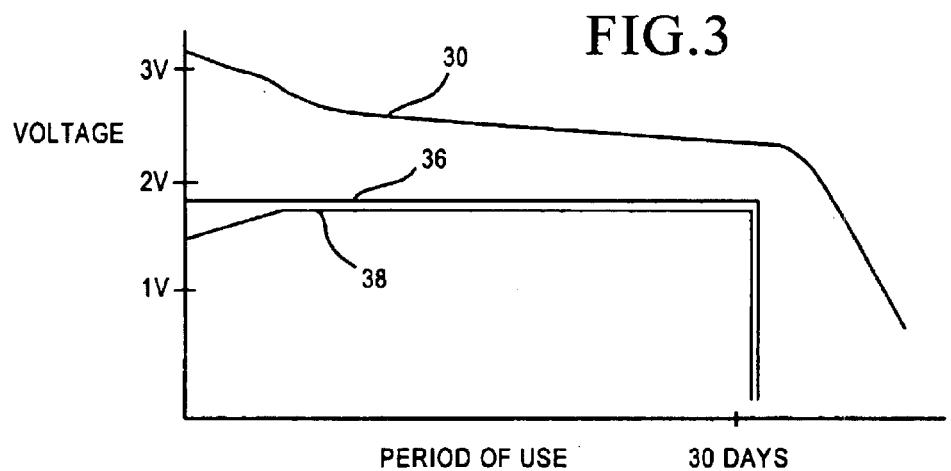
FIG. 3 shows a series of battery voltage discharge curves for the battery-powered toothbrush of FIG. 1.

Control of the power to the motor is an important aspect of the present invention. Referring to FIG. 3, voltage-discharge curve 30 is that of a typical alkaline battery alone, without any adjustment. An alkaline battery is desirable in the present invention because it will deliver approximately full power for a complete trial period of time (one month/30 days) and then decrease quite quickly in output, instead of a long, steady, slow decline. Hence, the device will actually cease to operate shortly after the battery begins to decrease from full power (at the end of the trial period), so that operation and performance is not impaired for a substantial period of time prior to the battery ceasing operation.

In the embodiment shown, two 1.5 volt alkaline batteries start out at approximately a total of 3 volts, and gradually decline to approximately 2.6 volts over their lifetime, at which point the voltage output drops rather quickly. This decline may begin to occur at approximately one month/30 days of brushing use (two brushing events per day at two minutes for each event). The alkaline batteries thus are generally capable of providing a power output level sufficient to emulate the operation and performance of the corresponding commercial toothbrush for a period of time appropriate for an adequate trial use of the toothbrush.

In the present invention, a power control circuit assists in providing a controlled level of power to the drive motor 18 from battery 16. In operation, the initial power output of battery 16 is decreased so that it coincides with the battery output of the corresponding commercial unit, i.e. 2.4 volts in the present embodiment. Briefly, the power control circuit controls the power to the drive motor by varying the duty cycle of its (the control circuit) output control signals. In the embodiment shown, the power from the 3.0 volt batteries is decreased by decreasing the duty cycle of the control signals to match the power produced by the 2.4 volt batteries in the commercial unit. It will then adjust the duty cycle of the control signals to maintain the power delivered to the motor over the life of the trial unit to approximate that of the commercial unit. Thus, for the desired useful life of the trial unit 10, the power to the motor is maintained substantially the same (a flat value, neither increasing nor decreasing), corresponding to that of the commercial unit.

The power control circuit is shown and described in U.S. Pat. No. 5,994,855 and in the simplified block diagram circuit of FIG. 3. The power control circuit includes a microcontroller 40 and a motor drive circuit 42. The microcontroller is programmed to control the duty cycle of the drive signals from the motor drive circuit 42 in such a manner that the power from the battery 16 is initially decreased to match the output of the commercial unit battery. The duty cycle is then gradually increased to compensate for any decrease in the battery voltage discharge value over time, maintaining the same power level over time, until a preselected number of uses of the trial unit has occurred, at which point the output drive signals from the motor drive circuit 42 are terminated, ending the usefulness of the trial unit. The microcontroller 40 is programmed with the known voltage discharge curve of the batteries, so that the change in duty cycle can match the change in battery voltage output over time. This is shown as voltage discharge curve 36 in FIG. 3.

Figure 2:
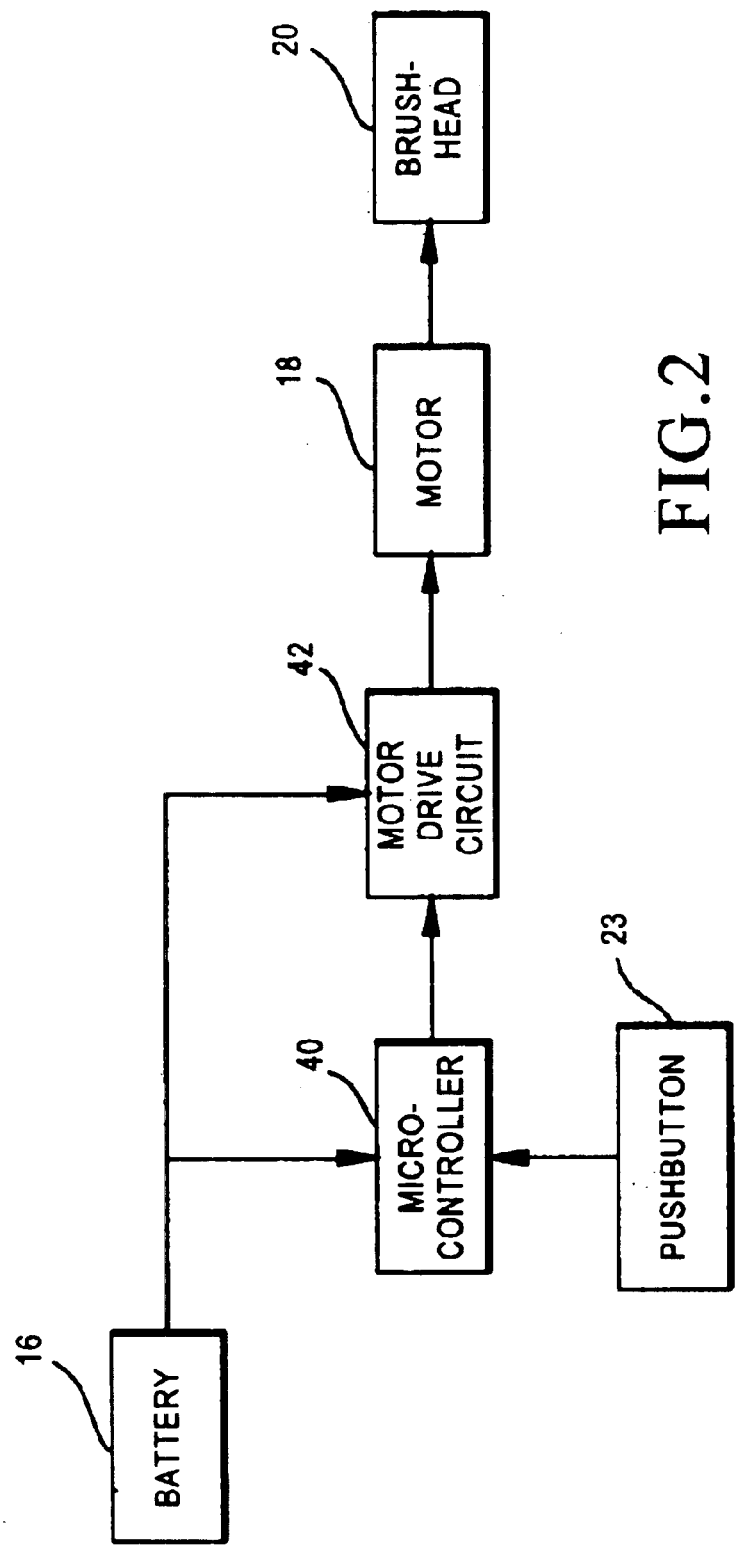
FIG. 2 shows a simplified block diagram of a power control circuit for the toothbrush of FIG. 1.

The actual termination of the drive signal by the control circuit of FIG. 2 is an alternative to the battery losing power sufficient to run the unit after a selected short period of time (the trial time). The drive signal termination circuit, while not necessary to the present invention, is in fact significant for a number of reasons, including ensuring that the trial unit will last for the desired number of brushings, but no more.

Regardless of whether the battery is allowed to decrease on its own through its normal voltage discharge cycle, wherein the unit stops functioning at a particular point in time, or its use is actually terminated, there must in both cases be a significant confidence, e.g. 95 percent, that the device will last with appropriate emulation of brushing effect for at least 60 brushings or some other specific number of brushings adequate to provide an appropriate trial use time for the unit.

Figure 4:
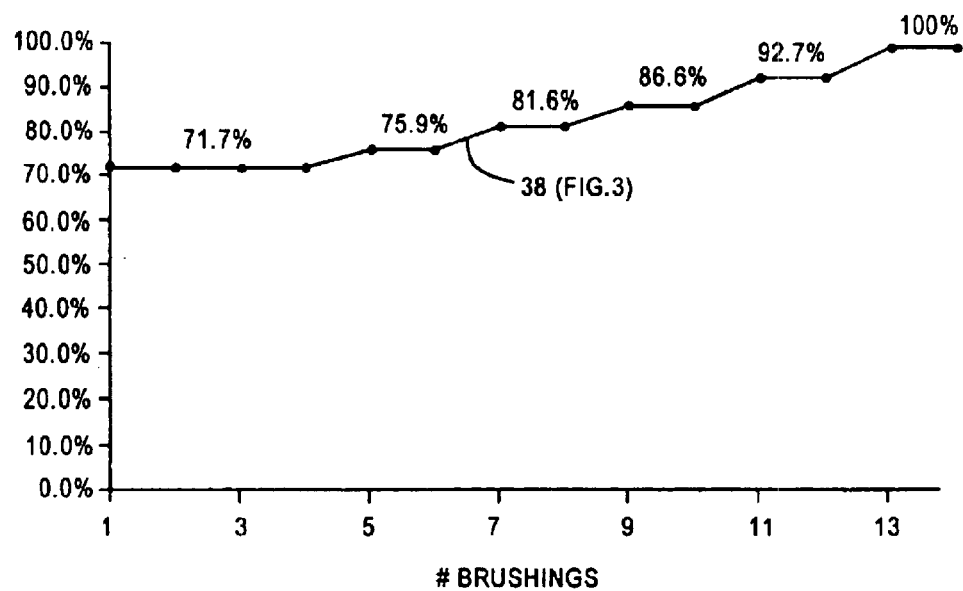
FIG. 4 shows a power curve for introductory use of a power toothbrush to accommodate the user to the toothbrush.

The voltage discharge line 38 shows another power dependent feature superimposed on the voltage discharge curve 36. In voltage discharge curve 38, the power control circuit initially reduces the drive signal from circuit 42 to a lower than full power level so as to permit the user to be acclimated to the operation of the device. An example of a very specific power ramp-up characteristic is shown in more detail in FIG. 4, in which the power to the motor 18 is increased from approximately 70% initial power to 100%, over a total of approximately 13 brushings. Other "ramp-up" characteristics can be used.

This arrangement permits the user to be gradually accommodated to the operation of the device. The power control circuit thus initially, through control of the duty cycle of drive circuit 42, provides a power output to the motor which is less than full power, i.e. less than the commercial unit at normal operation. After a selected limited number of brushings, however, full power is reached and the power control circuit then maintains a full power output to the motor 18 for the predetermined life of the trial unit. While this "learning feature" of initial lowered power is not necessary to the present invention, it does emulate another feature of operation of the corresponding commercial power toothbrush and therefore has been described herein.

Thus, in the particular embodiment shown, the power control circuit provides a motor drive signal which results in lower power to the motor at the beginning of the toothbrush trial time, but then ramping up to and thereafter maintaining full power until the end of life of the trial unit. As explained above, the end of life of the trial unit can be the result of the natural fast decrease in power of an alkaline battery after a selected number of uses or can result from an abrupt termination of power to the motor by operation of the power control unit itself.

Other features of the commercial unit, particularly those which affect brush performance, may be emulated. For instance, a blinking light indication for a low battery condition might be provided, among others.

At the end of the preselected number of uses, the appropriate time for use, the trial unit is no longer operative. The unit then may be disposed of by the user, without the inconvenience of having to return it to the manufacturer. This is a characteristic of most conventional trial units.

Hence, a trial unit for a corresponding commercial power toothbrush provides emulation of the commercial unit for a selected number of uses, to produce an adequate "trial" use of the commercial unit. The unit is designed to be disposable after the trial use. It includes low cost, non-rechargeable batteries and comes without any charging mechanism. The unit may be designed and packaged in particular ways to indicate that it is a test unit, and to reduce cost while still faithfully emulating the operation and performance of the corresponding commercial unit. This results in a satisfactory trial of the commercial device for a prospective customer. After experiencing the trial unit, the user then will most likely want to move directly toward purchase of the commercial unit (returning to previous manual brushing methods is usually not seen as desirable by the consumer). They can also be encouraged through various ways to purchase an actual commercial unit, such as through promotions, special discounts, etc. The trial unit, however, is not convertible into a commercial unit and is designed to be disposable. This basic "trial unit" concept may also be applicable to other power personal care items which may otherwise be seen as too expensive for trial units.

Although a preferred embodiment of the invention has been disclosed herein for purposes of illustration, it should be understood that various changes, modifications and substitutions may be made without departing from the spirit of the invention, which is defined by the claims which follow.

What is claimed is:

1. A trial-use power toothbrush, comprising:
    a trial power toothbrush designed to emulate the performance of a corresponding commercially available power toothbrush;
    a power system, including a battery, to provide power for the trial power toothbrush for only a selected short trial use period time which is long enough, approximately sixty brushings, for approximately one month of use, that the user becomes accommodated to the operation of the trial power toothbrush and can evaluate the performance thereof, but is substantially less than a normal period of use, wherein the trial power toothbrush approximates the operation of the corresponding commercial toothbrush for said selected period of time; and
    a control circuit, separate from the battery, preventing further operation of the power toothbrush at the end of said selected period of time.

2. An article of claim 1, wherein the power system includes a non-rechargeable battery.

3. An article of claim 2, wherein the non-rechargeable battery has a power discharge characteristic such that at the end of said short period of time, the voltage output from the battery is insufficient to operate the trial power toothbrush.

4. An article of claim 1, wherein the control circuit controls the power to operate the trial toothbrush at a level approximately that of the corresponding commercial toothbrush over said short period of time, based on the voltage output of the battery over the short period of time, including means for compensating for any decrease in voltage output of the battery over the short period of time.

5. An article of claim 1, wherein the control circuit provides lower than full power output to drive the toothbrush for a portion of time at the beginning of the short period of time so as to accommodate the user to operation of the toothbrush.

6. An article of claim 1, wherein the power toothbrush is conveniently disposable following the trial use thereof.

7. A trial-use power personal care appliance, comprising:
    a trial power personal care appliance designed to emulate the performance of a corresponding commercially available personal care appliance;
    a power system, including a battery, to provide power for the trial power appliance for only a selected short period of time which is long enough, approximately sixty uses, for approximately one month of use, that the user becomes accommodated to the operation of the trial power appliance and can evaluate the performance thereof, but substantially less than a normal period of use, wherein the trial power appliance approximates the operation of the corresponding commercial appliance for said selected period of time; and
    means, separate from the battery, preventing further operation of the personal care appliance at the end of said selected period of time.

8. An article of claim 7, wherein the power system includes a non-rechargeable battery.

9. An article of claim 8, wherein the preventing means includes a power control circuit which in combination with the battery controls the operation of the trial power appliance and terminates operation thereof following said selected period of time.

10. A trial-use power toothbrush, comprising:
    a trial power toothbrush designed to emulate the performance of a corresponding commercially available power toothbrush;
    a power system, including a battery, to provide power for the power toothbrush for only a selected trial use period of time which is long enough that the user becomes accommodated to the operation of the trial power toothbrush and can evaluate the performance thereof, but is substantially less than a normal period of use, wherein the power trial toothbrush approximates the operation of the corresponding commercial toothbrush for a selected period of time; and
    a control circuit, separate from the battery, preventing further operation of the power toothbrush at the end of said selected trial use period of time.

* * * * *